United States Patent
Ferlita et al.

(10) Patent No.: US 7,700,611 B2
(45) Date of Patent: Apr. 20, 2010

(54) SYNTHESIS AND CRYSTALLINE FORMS OF NPY5 ANTAGONIST

(75) Inventors: Russell R. Ferlita, Westfield, NJ (US); Yuji Haga, Tsukuba (JP); Makoto Ishikawa, Ushiku (JP); Keisuke Kamei, Isesaki (JP); Shinji Kato, Nagoya (JP); Hisaki Kojima, Nagoya (JP); Aaron Moment, Edison, NJ (US); Nobuaki Nonoyama, Chiryu (JP); Nobuya Satake, Okazaki (JP); Kazuki Shigemori, Anjyou (JP); Toshihiro Wada, Tsukuba (JP); Yaling Wang, Westfield, NJ (US); Steven A. Weissman, Short Hills, NJ (US); Robert M. Wenslow, Cream Ridge, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 64 days.

(21) Appl. No.: 11/988,780

(22) PCT Filed: Jul. 24, 2006

(86) PCT No.: PCT/US2006/028650
§ 371 (c)(1),
(2), (4) Date: Jan. 14, 2008

(87) PCT Pub. No.: WO2007/016028
PCT Pub. Date: Feb. 8, 2007

(65) Prior Publication Data
US 2009/0124648 A1    May 14, 2009

Related U.S. Application Data

(60) Provisional application No. 60/703,088, filed on Jul. 28, 2005.

(51) Int. Cl.
*A61K 31/4355* (2006.01)
*C07D 491/048* (2006.01)

(52) U.S. Cl. .......... 514/278; 546/15; 546/116; 514/302

(58) Field of Classification Search ............... 514/278, 514/302; 546/15, 116
See application file for complete search history.

(56) References Cited

U.S. PATENT DOCUMENTS 6,335,345 B1    1/2002    Fukami et al.

FOREIGN PATENT DOCUMENTS

| WO | WO 01/14376   | 3/2001  |
| WO | WO 2004/037170 | 5/2004  |
| WO | WO 2004/037794 | 5/2004  |
| WO | WO 2004/104009 | 12/2004 |

OTHER PUBLICATIONS

Iida et al., J. Org. Chem., vol. 70 (2005), pp. 9222-9229, "Practical synthesis of a neuropeptide Y antagonist via stereoselective addition to a ketene".

*Primary Examiner*—Charanjit S Aulakh
(74) *Attorney, Agent, or Firm*—Baerbel R. Brown; John C. Todaro (57) ABSTRACT

The present invention relates to a process for producing crystalline trans-N-[1-(2-fluorophenyl)-S-pyrazoly]-3-ox-ospiro[6-azaisobenzofuran-1(3H),1'-cyclohexane]-4'-carboxamide and novel salts, hydrates and polymorphs thereof.

19 Claims, 5 Drawing Sheets

SYNTHESIS AND CRYSTALLINE FORMS OF NPY5 ANTAGONIST

CROSS-REFERENCE TO RELATED APPLICATIONS

This application is a U.S. National Phase application under 35 U.S.C. § 371 of PCT Application No. PCT/US2006/028650, filed 24 Jul. 2006, which claims priority from and the benefit of U.S. Provisional Application No. 60/703,088, filed Jul. 28, 2005.

BACKGROUND OF THE INVENTION

U.S. Pat. No. 6,335,345 (issued Jan. 1, 2002) discloses the compound of structural formula I.

Compound I, and its novel polymorphic forms, are NPY5 antagonists useful as agents for the treatment of various diseases related to NPY, including, but not limited to, cardiovascular disorders, such as hypertension, nephropathy, heart disease, vasospasm, arteriosclerosis, central nervous system disorders, such as bulimia, depression, anxiety, seizure, epilepsy, dementia, pain, alcoholism, drug withdrawal, metabolic diseases such as obesity, diabetes, hormone abnormality, hypercholesterolemia, hyperlipidemia, hypertension, metabolic syndrome, sexual and reproductive dysfunction, gastrointestinal disorder, respiratory disorder, inflammation and glaucoma.

A novel process for the preparation of Compound I was disclosed in WO 01/14376 (published 1 Mar. 2001). The disclosed coupling process employed EDC-HCl and required the separate free base formation step of the pyrazole salt prior to use. Safety and cost concerns associated with the EDC-HCl route led to the development of the present route, which used thionyl chloride as an improved reagent for the transformation and in which the free base step is performed in-situ. The yield of the improved streamlined process is comparable to the original process.

The original process for the preparation of Compound I, as disclosed in WO 01/14376, yielded Compound I as a mixture of crystalline Form A and amorphous compound. However, the instability of Form A at room temperature complicated the development of solid dosage formulations for compound I. It is therefore desirable to have available other crystalline forms of Compound I having improved stability for the preparation of a solid pharmaceutical dosage form containing Compound I as the active pharmaceutical ingredient. There is no specific disclosure or discussion of pure crystalline Form A, crystalline Form C or the crystalline mesylate and fumarate salts of compound I in U.S. Pat. No. 6,335,345 or WO 01/14376.

SUMMARY OF THE INVENTION

This invention provides a process for producing trans-N-[1-(2-fluorophenyl)-3-pyrazolyl]-3-oxospiro[6-azaisobenzofuran-1(3H),1'-cyclohexane]-4'-carboxamide of structural formula I from spirolactone II and pyrazole III.

This invention further provides four novel crystalline forms of N-[1-(2-fluorophenyl)-3-pyrazolyl]-3-oxospiro[6-azaisobenzofuran-1(3H), 1'-cyclohexane]-4'-carboxamide that have been identified are designated pure Form A, Form C, the mesylate salt and the fumarate salt. Forms A and C are crystalline anhydrous polymorphs of the free base of Compound I. The crystalline forms of these polymorphs are new and may have advantages in the preparation of pharmaceutical compositions of Compound I, such as ease of processing, handling and dosing. The novel crystal Form C is the most thermodynamically stable crystalline form of Compound I below 81° C., while the most thermodynamically stable crystalline form of compound (I) above 81° C. is Form A. The most thermodynamically stable crystalline form at room temperature (22° C.), Form C, consists of bulk material with crystal homogeneity that is not subject to transforming to another crystal form, such as form A, on storage. In particular, crystalline Form C is more thermodynamically stable at room temperature rendering it particularly suitable for the manufacture of pharmaceutical dosage forms.

The present invention also relates to pharmaceutical formulations comprising the novel polymorphs and salts of compound I as active pharmaceutical ingredients, as well as methods for using them as NPY5 antagonists in the treatment of NPY5 related disorders.

DETAILED DESCRIPTION OF THE INVENTION

The present invention provides a process for the preparation of trans-N-[1-(2-fluorophenyl)-3-pyrazolyl]-3-oxospiro[6-azaisobenzofuran-1(3H),1'-cyclohexane]-4'-carboxamide of structural formula (I)

and crystalline polymorphs and salts thereof.

Compound I can be prepared by employing the following General Scheme, which shows the formation of Compound I via the reaction of spirolactone acid II with pyrazole III. International Patent Publications WO 04/037170 and WO 04/104009 disclose the preparation of spirolactone II; and WO 2004037794 discloses the preparation of pyrazole III.

GENERAL SCHEME

Figure 1:
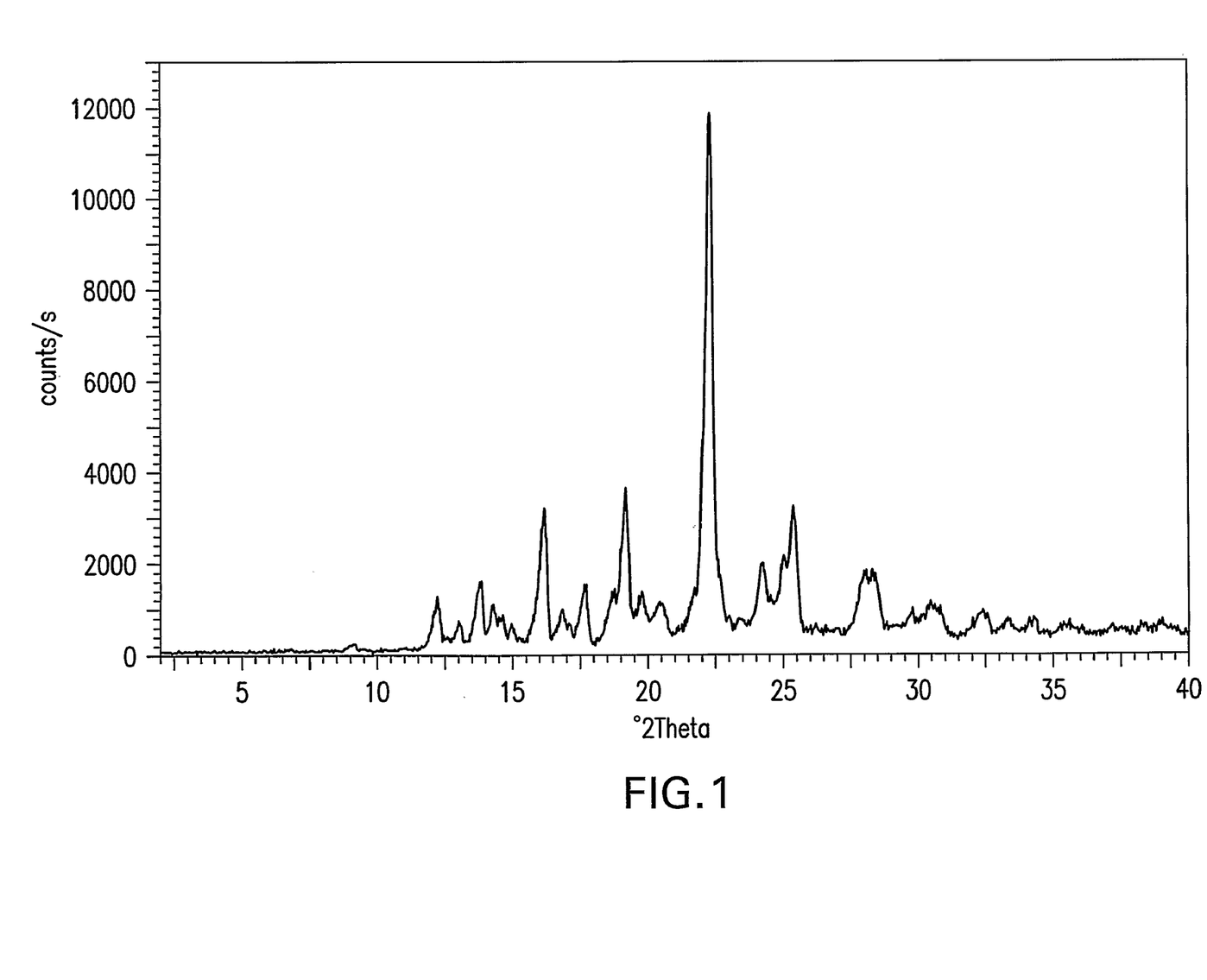
FIG. 1 is the X-ray diffraction (XRPD) pattern for Compound I polymorphic Form A.

The free base of compound I has two known crystalline polymorphs denoted as Form A and Form C. These two polymorphs have an enantiotropic transition at approximately 81° C. Compound I can be recrystallized to form polymorph form C and may be converted from Form C to Form A at temperatures greater than 81° C. The X-ray powder diffraction (XPRD) patterns for the two free base anhydrous crystalline Forms of Compound I are shown in FIG. 1 (Form A) and FIG. 2 (Form C). The thermogravimetric analysis (TGA) curve obtained on Compound I Form C, under nitrogen flow at a heating rate of 10° C./minute, showed a 0.5% weight loss from room temperature to approximately 250° C.

Figure 2:
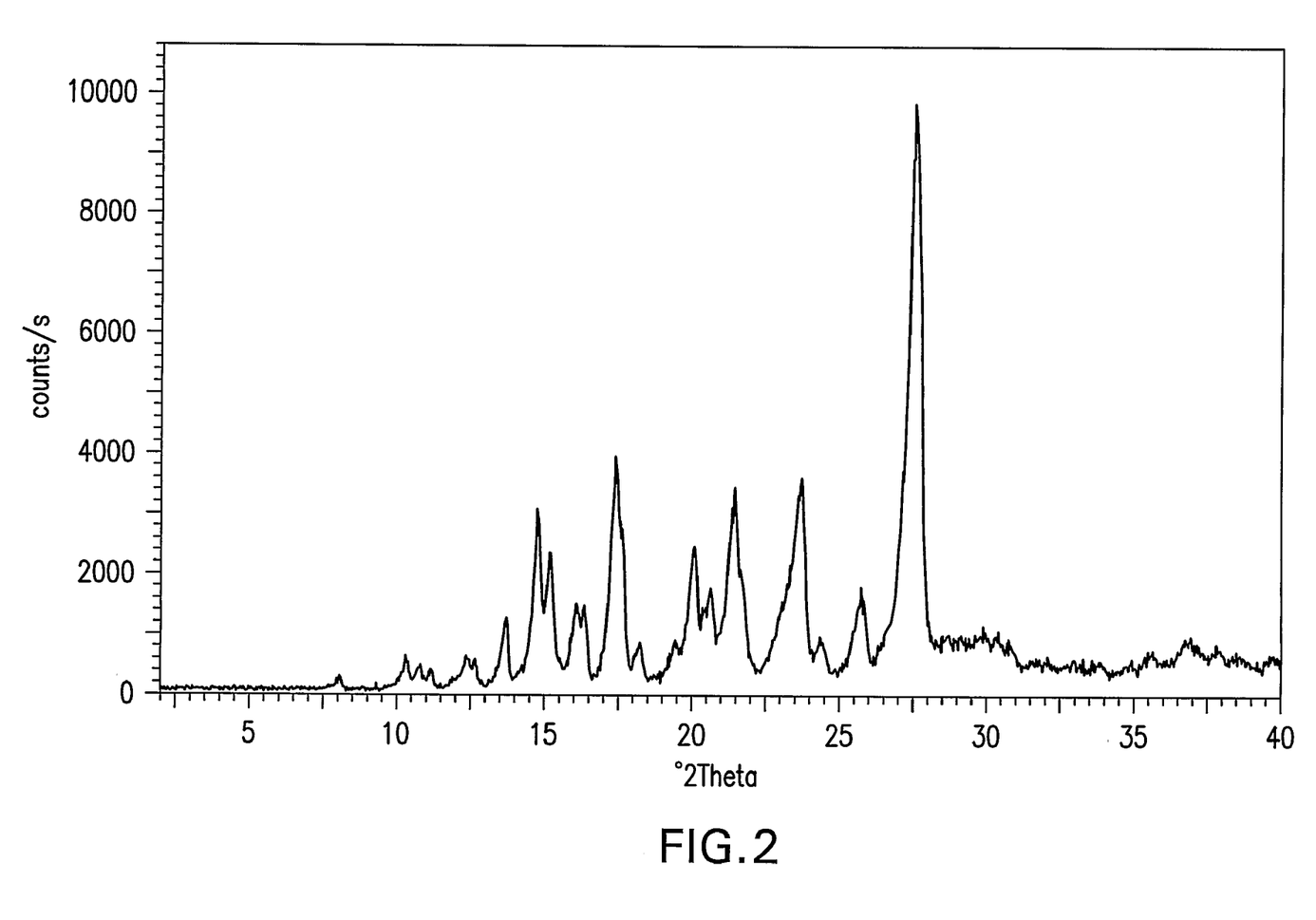
FIG. 2 is the X-ray diffraction (XRPD) pattern for Compound I polymorphic Form C.

The DSC curve is characterized by two endotherms: the first endotherm is due to the transition of Form C, the low temperature stable polymorph, to Form A, the high temperature stable polymorph. The first endotherm, which is due to Form C, has an extrapolated onset temperature of 212.8° C., a peak temperature of 216.7° C., and an associated heat of 11.8 J/g. The second endotherm is due to the melting of Form A, and has an extrapolated onset temperature of 237.5° C., a peak temperature of 238.5° C. and an associated heat of 108.8 J/g.

Figure 3:
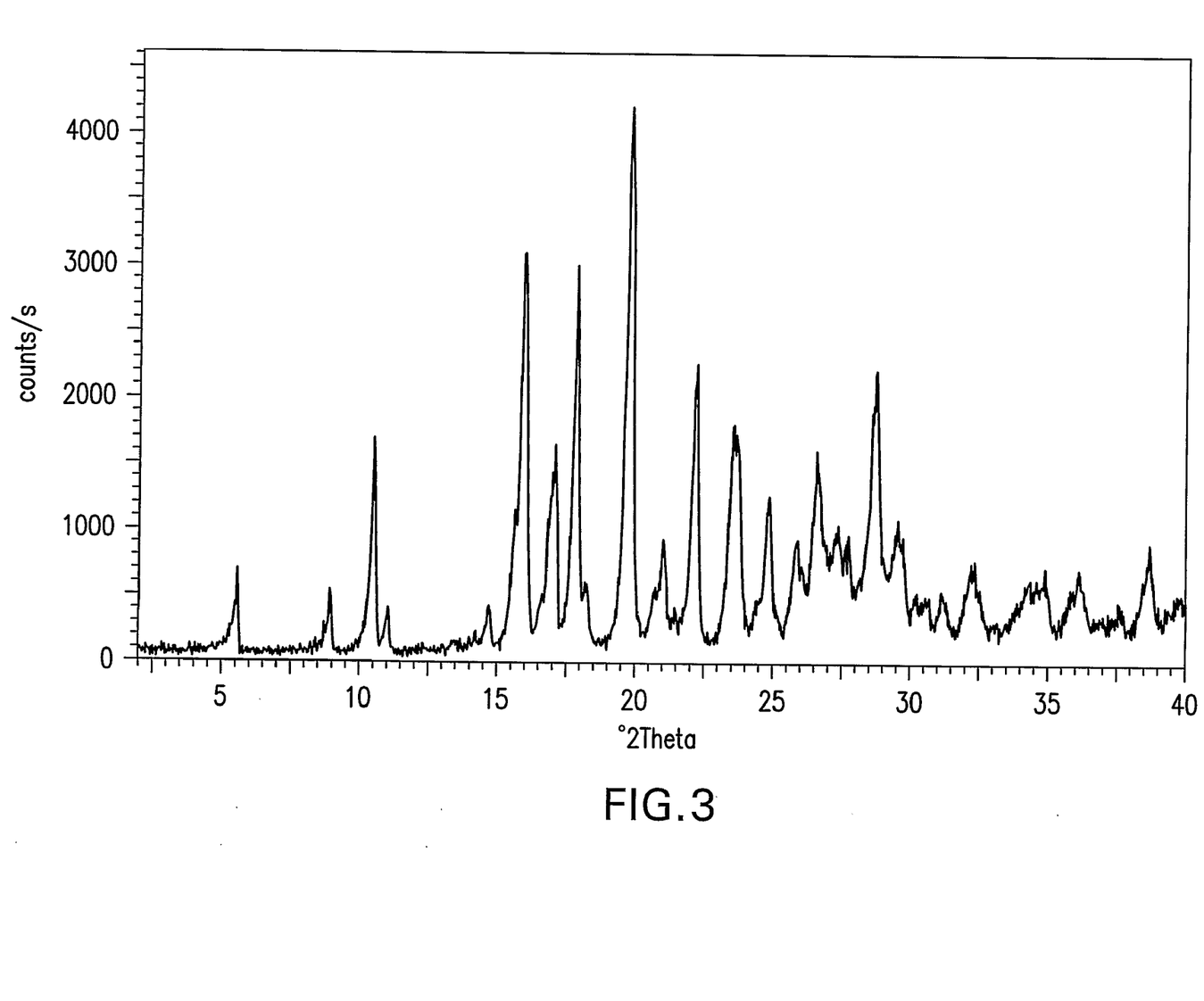
FIG. 3 is the X-ray diffraction (XRPD) pattern for the crystalline mesylate salt of Compound I.
Figure 4:
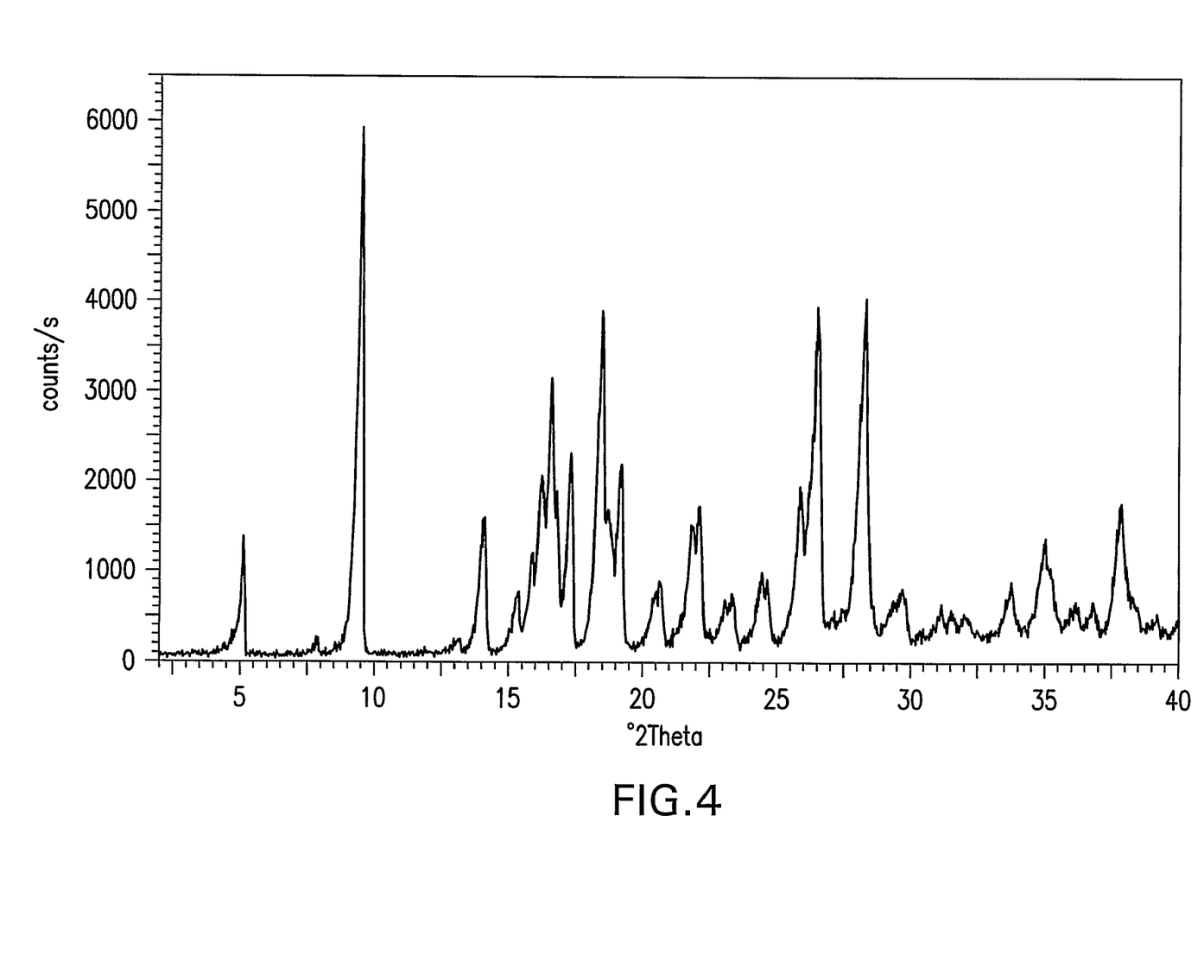
FIG. 4 is the X-ray diffraction (XRPD) pattern for the crystalline fumarate salt of Compound I.

Compound I may further be converted to the crystalline mesylate and fumarate salts as described below. FIG. 3 shows the X-ray diffraction pattern of the mesylate salt of Compound I, and FIG. 4 shows the X-ray diffraction pattern of the fumarate salt of Compound I. The mesylate salt has been found to disproportionate to polymorphic Form A upon contact with water, while the fumarate salt has been found to disproportionate to the free base of Compound I upon contact with water.

One embodiment of the present invention provides a process for preparing a compound of formula I, or a salt, hydrate or polymorph thereof, comprising the step of coupling a compound of formula II with a compound of formula III, or a salt thereof, in the presence of $SOCl_2$ and dimethylacetamide.

In a class of this embodiment, the salt of the compound of formula III is selected from the group consisting of: the hydrochloride salt and the toluenesulfonic acid salt. In yet another class of this embodiment, the salt of the compound of formula III is the toluenesulfonic acid salt. In a subclass of this class, the salt of the compound of formula III is the hydrochloride salt. In another subclass of this class, the salt of the compound of formula III is the toluenesulfonic acid salt.

In a class of this embodiment, the process further comprises isolating the compound of formula I. In a subclass of this class, the compound of formula I is isolated by recrystallizing from dimethyl formamide, methanol and deionized water. In a subclass of this subclass, the water is de-ionized water. In another subclass of this class, the compound of formula I is isolated by recrystallizing from dimethylacetamide and water. In a subclass of this subclass, the water is de-ionized water.

Another embodiment of the present invention provides for a method of preventing or treating obesity or an obesity related disorder comprising administering a therapeutically effective amount of a polymorph, hydrate or salt of Compound I to a subject in need thereof.

The use of a therapeutically effective amount of a polymorph, hydrate or salt of Compound I for the manufacture of a medicament useful for the treatment, control, or prevention of obesity or an obesity-related disorder in a subject in need of such treatment.

The term "trans-N-[1-(2-fluorophenyl)3-pyrazolyl]-3-oxospiro[6-azaisobenzofuran-1(3H),1'-cyclohexane]-4'-carboxamide" comprises not only the solid form of trans-N-[1-(2-fluorophenyl)-3-pyrazolyl]-3-oxospiro[6-azaisobenzofuran-1(3H),1'-cyclohexane]-4'-carboxamide, but also any amorphous or partially crystalline solid form of trans-N-[1-(2-fluorophenyl)-3-pyrazolyl]-3-oxospiro[6-azaisobenzofuran-1(3H),1'-cyclohexane]-4'-carboxamide, such as glasses, lyophilates, and mixtures thereof, which may be converted to trans-N-[1-(2-fluorophenyl)-3-pyrazolyl]-3-oxospiro[6-azaisobenzofuran-1(3H),1'-cyclohexane]-4'-carboxamide through warming.

Polymorphs are compounds having the same chemical composition but different crystal structures. Polymorphism is the ability of the same chemical substance to exist as different crystalline structures. The trans-N-[1-(2-fluorophenyl)-3-pyrazolyl]-3-oxospiro[6-azaisobenzofuran-1(3H),1'-cyclohexane]-4'-carboxamide of structural formula I has been found it exist in at least two polymorphic forms, Form A and Form C, each of which can be formed by careful control of the crystallization conditions.

The term "hydrate" is meant to include all full, multiple and partial hydrates of compound I, including, but not limited to, the mono hydrate, hemi-hydrate and bis hydrate.

The term "solvate" is meant to include compound forms containing solvent molecules within the crystal structure of Compound I, or solvent molecules bound to or associated with Compound I, including but not limited to acetonitrile and methanol.

The term "amorphous" refers to solid forms that have no long-range molecular order.

The trans-N-[1-(2-fluorophenyl)-3-pyrazolyl]-3-oxospiro[6-azaisobenzofuran-1(3H),1'-cyclohexane]-4'-carboxamide of structural formula I has been found to form crystalline mesylate and fumarate salts.

Additional salts of compounds of formula I refer to the pharmaceutically acceptable and common salts, for example, base addition salt to carboxyl group when the compound has a carboxyl group, or acid addition salt to amino or basic heterocycle when the compound has an amino or basic heterocycle group, and the like. The term "pharmaceutically acceptable salts" refers to salts prepared from pharmaceutically acceptable non-toxic bases or acids including inorganic bases or acids and organic bases or acids. The base addition salts include salts with alkali metals (including, but not limited to, sodium, potassium); alkaline earth metals (including, but not limited to, calcium, magnesium); ammonium or organic amines (including, but not limited to, trimethylamine, triethylamine, dicyclohexylamine, ethanolamine, diethanolamine, triethanolamine, procaine, N,N'-dibenzylethylenediamine), and the like. The acid addition salts include salts with inorganic acids (including, but not limited to, hydrochloric acid, sulfuric acid, nitric acid, phosphoric acid, perchloric acid), organic acids (including, but not limited to, acetic acid, oxalic acid, maleic acid, fumaric acid, tartaric acid, citric acid, ascorbic acid, trifluoroacetic acid, acetic acid), sulfonic acids (including, but not limited to, methanesulfonic acid, isethionic acid, benzenesulfonic acid, p-toluenesulfonic acid, p-toluenesulfonic acid monohydrate, p-toluene sulfonic acid hydrate, camphor sulfonic acid), and the like.

In one embodiment of the present invention there is provided a pharmaceutical composition comprising trans-N-[1-(2-fluorophenyl)-3-pyrazolyl]-3-oxospiro[6-azaisobenzofuran-1(3H),1'-cyclohexane]-4'-carboxamide (Compound I) as a free base, salt, hydrate or polymorph thereof. In a class of this embodiment, the composition comprises trans-N-[1-(2-fluorophenyl)-3-pyrazolyl]-3-oxospiro[6-azaisobenzofuran-1(3H),1'-cyclohexane]-4'-carboxamide (Compound I) as polymorph Form A or Form C, or a combination thereof. In a subclass of this class, the composition comprises trans-N-[1-(2-fluorophenyl)-3-pyrazolyl]-3-oxospiro[6-azaisobenzofuran-1(3H),1'-cyclohexane]-4'-carboxamide (Compound I) as polymorph Form C. In a subclass of this class, the polymorphic Form C is in substantially pure form. In another subclass of this class, the composition comprises trans-N-[1-(2-fluorophenyl)-3-pyrazolyl]-3-oxospiro[6-azaisobenzofuran-1(3H),1'-cyclohexane]-4'-carboxamide (Compound I) as polymorph Form A. In a subclass of this class, the polymorphic Form A is in substantially pure form. In another class of this embodiment, the composition comprises trans-N-[1-(2-fluorophenyl)-3-pyrazolyl]-3-oxospiro[6-azaisobenzofuran-1(3H),1'-cyclohexane]-4'-carboxamide (Compound I) as the fumarate salt. In a subclass of this class, the fumarate salt is crystalline. In another class of this embodiment, the composition comprises trans-N-[1-(2-fluorophenyl)-3-pyrazolyl]-3-oxospiro[6-azaisobenzofuran-1(3H),1'-cyclohexane]-4'-carboxamide (Compound I) as the mesylate salt. In a subclass of this class, the mesylate salt is crystalline.

The compounds in the processes of the present invention include stereoisomers, such as optical isomers, diastereomers and geometerical isomers, or tautomers depending on the mode of substitution. The present invention is meant to comprehend all such isomeric forms of the compounds in the compositions of the present invention, and their mixtures. All hydrates, solvates and polymorphic crystalline forms of the above-described compounds and their use, including their use in the processes of the instant invention, are encompassed within scope of the instant invention.

Another aspect of the present invention provides pharmaceutical compositions which comprises a polymorph, hydrate or salt of Compound I and a pharmaceutically acceptable carrier. The pharmaceutical compositions of the present invention comprise a compound of Formula I as an active ingredient or a pharmaceutically acceptable salt thereof, and may also contain a pharmaceutically acceptable carrier and optionally other therapeutic ingredients.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the polymorphs, hydrates and salts of Compound I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

The polymorphs, hydrates and salts of Compound I may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

The present invention provides a method for the treatment and/or prevention of obesity and obesity-related disorders in a subject in need thereof comprising administering a therapeutically effective amount of a hydrate, salt or polymorph of Compound I to the subject in need thereof. The present invention also provides for the use of the hydrates, salts and polymorphs of Compound I for the manufacture of a medicament for the prevention and/or treatment of obesity and obesity related disorders.

The obesity-related disorders herein are associated with, caused by, or result from obesity. Examples of obesity-related disorders include restenosis, atherosclerosis, arteriosclerosis, overeating and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrhythmias, myocardial infarction, congestive heart failure, coronary heart disease, sudden death, stroke, polycystic ovary disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g., children with acute lymphoblastic leukemia, metabolic syndrome, insulin resistance syndrome, reproductive hormone abnormalities, sexual and reproductive dysfunction, such as impaired fertility, infertility, hypogonadism in males and hirsutism in females, fetal defects associated with maternal obesity, gastrointestinal motility disorders, such as obesity-related gastro-esophageal reflux, respiratory disorders, such as obesity-hypoventilation syndrome (Pickwickian syndrome), breathlessness, cardiovascular disorders, inflammation, such as systemic inflammation of the vasculature, arteriosclerosis, hypercholesterolemia, hyperuricaemia, lower back pain, gallbladder disease, gout, kidney cancer, increased anesthetic risk, left ventricular hypertrophy, Alzheimer's disease.

"Treatment" (of obesity and obesity-related disorders) refers to the administration of the compounds or combinations of the present invention to reduce or maintain the body weight of an obese subject. "Prevention" (of obesity and obesity-related disorders) refers to the administration of the compounds or combinations of the present invention to reduce or maintain the body weight of a subject at risk of obesity.

The term "subject", as used herein refers to an animal, preferably a mammal, most preferably a human, who has been the object of treatment, observation or experiment. The term "subject in need thereof" refers to a subject who is in need of treatment or prophylaxis as determined by a researcher, veterinarian, medical doctor or other clinician. In one embodiment, the subject in need of treatment is an obese mammal. In another embodiment, the subject in need of treatment is an obese human with one or more obesity-related co-morbidities. In another embodiment, the subject in need of treatment is an obese human without obesity-related co-morbidities. The term "therapeutically effective amount" as used herein means the amount of the active compounds in the composition that will elicit the biological or medical response in a tissue, system, subject, or human that is being sought by the researcher, veterinarian, medical doctor or other clinician, which includes alleviation of the symptoms of the disorder being treated.

The magnitude of prophylactic or therapeutic dose of the salt, hydrate or polymorph of compound I will, of course, vary with the nature of the severity of the condition to be treated and with the particular compound in the composition and its route of administration. It will also vary according to the age, weight and response of the individual patient. In general, for treating obesity or an obesity-related disorder, the daily dose range of a salt, hydrate or polymorph of compound I is administered at a daily dosage of from about 0.0001 mg/kg to about 100 mg/kg, preferably from about 0.001 mg/kg to about 50 mg/kg, more preferably from about 0.001 mg/kg to about 10 mg/kg of body weight body weight of a subject in single or divided doses two to six times a day, or in sustained release form. On the other hand, it may be necessary to use dosages outside these limits in some cases. The compounds of this invention can be administered to humans in the dosage ranges specific for each compound. For oral administration, the compositions are preferably provided in the form of tablets containing from 0.01 mg to 1,000 mg, preferably 0.01, 0.05, 0.1, 0.2, 0.5, 1.0, 2.5, 5, 10, 15, 20, 25, 30, 40, 50, 60, 75, 80, 100, 125, 150, 175, 200, 225, 250, 500, 750, 850 and 1,000 milligrams of each active ingredient for the symptomatic adjustment of the dosage to the subject to be treated. This dosage regimen may be adjusted to provide the optimal therapeutic response.

The X-ray powder diffraction pattern of the crystalline forms of trans-N-[1-(2-fluorophenyl)-3-pyrazolyl]-3-oxospiro[6-azaisobenzofuran-1(3H),1'-cyclohexane]-4'-carboxamide (Compound I) were generated on a Phillips XRG3100 X-ray diffractometer. A ceramic Cu LEF X-ray tube K-Alpha radiation was used as the source. The XRPD scan was run at ambient temperature.

DSC data were acquired using TA Instruments DSC 2910 or equivalent instrumentation. Between 2 and 6 mg sample is weighed into an open aluminum pan. This pan is then crimped and placed at the sample position in the calorimeter cell. An empty pan is placed at the reference position. The calorimeter cell is closed and a flow of nitrogen is passed through the cell. The heating program is set to heat the sample at a heating rate of 10° C./min to a temperature of approximately 250° C. The heating program is started. When the run is completed, the data are analyzed using the DSC analysis program contained in the system software. The melting endotherm is integrated between baseline temperature points that are above and below the temperature range over which the endotherm is observed. The data reported are the onset temperature, peak temperature and enthalpy.

TGA data were acquired using Perkin Elmer TGA7 thermogravimetric analyzer. Between 5 and 20 mg sample is weighed into a platinum pan. The furnace is raised and a flow of nitrogen is passed over the sample. The heating program is set to heat the sample at a heating rate of 10° C./min to a temperature of approximately 250° C. The heating program is started. When the run is completed, the data are analyzed using the delta Y function in the analysis program contained in the system software. The percent weight loss by the sample is calculated from the onset of the heating program to the melt/decomposition of the sample.

In addition to the X-ray powder diffraction patterns described above, the crystalline Form C of Compound I was further characterized by solid-state carbon-13 nuclear magnetic resonance (NMR) spectra. The solid-state carbon-13 NMR spectrum was obtained on a Bruker DSX 500WB NMR system using a Bruker 4 mm triple resonance CPMAS probe. The carbon-13 NMR spectrum utilized proton/carbon-13 cross-polarization magic-angle spinning with variable-amplitude cross polarization and SPINAL 64 proton decoupling at 100 kHz. Total sideband suppression was also implemented. The sample was spun at 10.0 kHz, and a total of 2048 scans were collected with a recycle delay of 120 seconds. A line broadening of 20 Hz was applied to the spectrum before FT was performed. Chemical shifts are reported on the TMS scale using the carbonyl carbon of glycine (176.03 p.p.m.) as a secondary reference.

In the schemes and examples below, various reagent symbols and abbreviations have the following meanings: DI water is deionized water; DMAc is dimethylacetamide; DMF is dimethylformamide; h is hour(s); HCl is hydrochloric acid, MeOH is methanol; min is minute(s); $SOCl_2$ is thionyl chloride; and TsOH is toluenesulfonic acid.

A representative experimental procedure utilizing the novel process is detailed below. The following Example is provided to illustrate the invention and is not to be construed as limiting the scope of the invention in any manner.

EXAMPLE 1

Preparation of trans-N-[1-(2-fluorophenyl)-3-pyrazolyl]-3-oxosiro[6-azaisobenzofuran-1(3H),1'-cyclohexane]-4'-carboxamide (Compound I) Free Base Polymorphic Form C

II

Step A Pyrazole TsoH Solution Preparation DMAc is charged to an empty, inert vessel followed by pyridine (3.65 eq. vs. Compound II). The pyrazole solids are charged (1.08 eq. vs. Compound II), and the vessel is rinsed with DMAc. The total DMAc charge for this preparation is 2.80 L/kg Compound II.

Step B Acid Chloride Formation/Coupling DMAc is charged to an empty, inert vessel. The spirolactone acid solids are charged, and the vessel is rinsed with DMAc. Compound II serves as the charge basis for the batch. The total DMAc charge for this preparation is 8.00 L/kg Compound II. The Compound II solution is cooled to −10 to −15° C., and thionyl chloride is slowly charged (1.05 eq. vs. Compound II), maintaining the batch below −10° C. Next, the pyrazole TsOH solution is slowly charged, maintaining the batch below −10° C. The batch is quenched with DI water (0.50 L/kg Compound II) at −10 to −15° C. and then warmed to 53 to 55° C. A DMAc flush (0.25 L/kg Compound II) follows the line filtration.

Step C Crystallization DI water (1.07 L/kg Compound II) is charged to reach the seed point, and the batch is warmed to 66 to 68° C. The batch is held in this range for 15 minutes and then cooled to 53 to 55° C. The batch is then seeded with milled material (3.0 wt. % Compound I Form C) and aged for 30 minutes. DI water is charged as the anti-solvent in three stages over 6.5 hours. The batch is cooled to 20 to 22° C. over 1 hour, aged for 30 minutes, and filtered. The batch is washed with DI water (5.00 L/kg Compound II), methanol (5.00 L/kg PY Acid), and methanol (3.50 L/kg Compound II) before being dried under vacuum at 50 ° C. to give Compound I as polymorphic Form C (>99 wt. % purity).

$^1$H NMR (400 MHz, DMSO-$d_6$): 10.82 (s, 1H), 9.13 (s, 1H), 8.89 (d, J=4.8 Hz, 1 H), 8.10 (t, J=2.6 Hz, 1H), 7.86 (dd, J=4.9, 1.1 Hz, 1H), 7.75 (td, J=7.8, 2.2 Hz, 1H), 7.47-7.40 (m, 1H), 7.40-7.30 (m, 2H), 6.91 (d, J=2.6 Hz), 2.21-1.96 (m, 6H), 1.96-1.85 (m, 2H).

TABLE 1

Powder X-ray diffraction: Compound I Crystal Form C

| 2θ(2 theta)(degrees) | Intensity(cps) | d-spacing (A) |
|---|---|---|
| 14.867 | 30.94 | 5.953 |
| 17.472 | 40.15 | 5.071 |
| 17.718 | 26.20 | 5.001 |
| 20.162 | 24.02 | 4.400 |
| 21.511 | 35.03 | 4.127 |
| 23.788 | 35.69 | 3.737 |
| 27.589 | 100.00 | 3.230 |

Although Compound I Form C is characterized by the complete group of angle 2 theta values listed in Table 1, all the values are not required for such identification. Compound I Form C can be identified by the angle theta value in the range of 27.0-28.0°. Compound I Form C can be identified by any one of the following angle theta values, or any one of the following groups of angle theta values:

a) 27.59°;

b) 27.6° and 17.5° c) 27.6°, 17.5° and 23.8° d) 27.6°, 17.5°, 23.8° and 21.5° e) 27.6°, 17.5°, 23.8°, 21.5°, and 14.9° f) 27.6°, 17.5°, 23.8°, 21.5°, 14.9°, 17.7°, and 20.2°

Additionally, each of the angle 2 theta values from Table 1 can be expressed to two decimal places as follows: 14.86°, 17.47°, 17.72°, 20.16°, 21.51°, 23.79°, and 27.59°.

Compound I Form C can also be identified by any one of the following d-spacings, or any one of the following groups of d-spacings, from an x-ray powder diffraction pattern obtained using Cu radiation:

a) 3.2, 5.1 and 3.7 angstroms;

b) 4.1, 5.9 and 5.0 angstroms; and c) 4.4 angstroms.

The thermogravimetric analysis (TGA) curve obtained on Compound I Form C, under nitrogen flow at a heating rate of 10° C./minute using a Perkin Elmer TGA7 thermogravimetric analyzer, showed a 0.5% weight loss from room temperature to approximately 250° C. Compound I Form C is also characterized by differential scanning calorimetry (DSC). The differential scanning calorimetry (DSC) curve for Compound I Form C, obtained under a nitrogen flow at a heating rate of 10° C./minute in an open cup using a TA Instruments 2920 calorimeter, is characterized by two endotherms. The first is due to a transition Form C, the low temperature stable polymorph, to Form A, the high temperature stable polymorph (this transformation was confirmed by XRPD). The first endotherm has an extrapolated onset temperature of 212.8° C., a peak temperature of 216.7° C.±2° C., and an associated heat of 11.8 J/g. This endotherm falls at a different temperature than the transition determined by the van't Hoff plot due to hysteresis. The second endotherm is due to the melt of Form A, with an extrapolated onset temperature of 237.5° C., a peak temperature of 238.5° C. and an associated heat of 108.8 J/g.

Compound I Form C can be identified by any one of the following carbon-13 cross-polarization magic-angle spinning (CPMAS) nuclear magnetic resonance (NMR) peaks in Table 2 (or FIG. 5), or any one of the following groups of carbon-13 cross-polarization magic-angle spinning (CP-MAS) nuclear magnetic resonance (NMR) peaks:

TABLE 2

Carbon-13 cross-polarization magic-angle spinning (CPMAS) nuclear magnetic resonance (NMR): Compound I Crystal Form C

Figure 5:
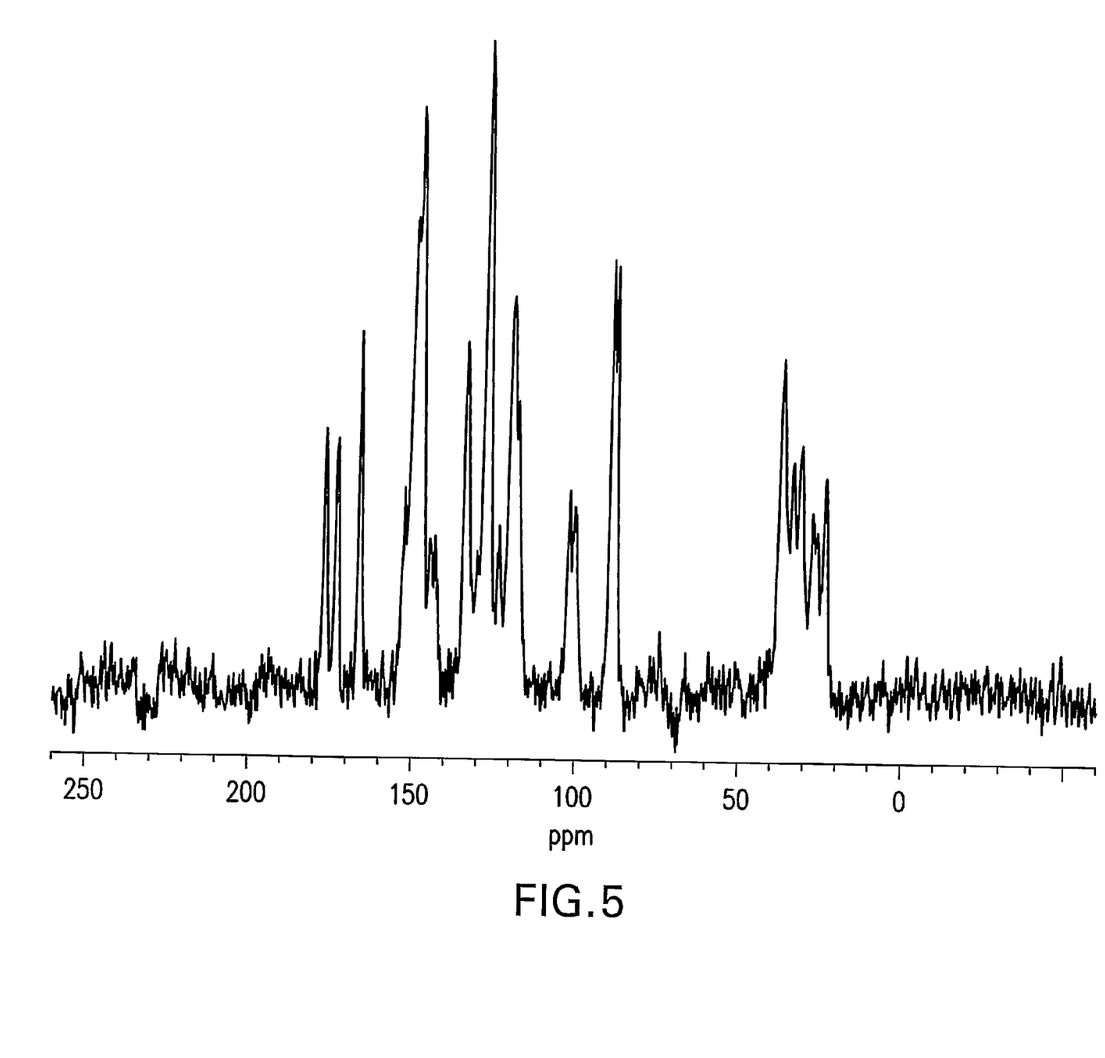
FIG. 5 is a carbon-13 cross-polarization magic-angle spinning (CPMAS) nuclear magnetic resonance (NMR) spectrum of the crystalline Form C of Compound I.

| Position (PPM) | Intensity (relative) |
|---|---|
| 176.3 | 40.0 |
| 172.7 | 38.5 |
| 165.8 | 55.0 |
| 152.3 | 30.9 |
| 147.8 | 89.8 |
| 143.1 | 23.4 |
| 133.5 | 53.6 |
| 127.1 | 100.0 |
| 123.2 | 25.1 |
| 119.4 | 60.9 |
| 101.5 | 30.7 |
| 100.0 | 28.3 |
| 88.7 | 66.9 |
| 87.3 | 65.8 |
| 73.3 | 9.1 |
| 36.2 | 51.7 |
| 32.8 | 35.5 |
| 30.4 | 38.2 |
| 27.0 | 27.7 |
| 22.8 | 33.0 |

EXAMPLE 2

Preparation of Crystalline trans-N-[1-(2-fluorophenyl)-3-pyrazolyl]-3-oxospiro[6-azaisobenzofuran-1(3H),1'-cyclohexane]-4'-carboxamide (Compound I) Polymorphic Form A Compound I polymorphic form C heated to 200° C. will convert to compound I polymorphic Form A.

The mesylate salt disproportionates to the free base Compound I Form A upon swishing in water for 3 hours.

TABLE 3

Powder X-ray diffraction: Compound I Crystal Form A

| 2θ(2 theta)(degrees) | Intensity(cps) | d-spacing (A) |
|---|---|---|
| 16.305 | 25.47 | 5.43 |
| 19.309 | 32.21 | 4.59 |
| 22.424 | 100.00 | 3.96 |
| 24.376 | 15.26 | 3.64 |
| 25.049 | 17.08 | 3.55 |
| 25.528 | 23.02 | 3.48 |

Although Form A of Compound I is characterized by the complete group of angle 2 theta values listed in Table 3, all the values are not required for such identification. Form A of Compound I can be identified by the angle theta value in the range of 22.0-23.0°. Form A of Compound I can be identified by any one of the following angle theta values, or any one of the following groups of angle theta values:

a) 22.42°;

b) 22.4° and 19.3° c) 22.4°, 19.3° and 16.3° d) 22.4°, 19.3°, 16.3° and 25.5° e) 22.4°, 19.3°, 16.3°, 25.5°, and 24.4° f) 22.4°, 19.3°, 16.3°, 25.5°, 25.0°, and 24.4°

Additionally, each of the angle 2 theta values from Table 3 can be expressed to two decimal places as follows: 16.30°, 19.30°, 22.42°, 24.37°, 25.04°, and 25.52°.

Compound I Form A can also be identified by one or more reflections at d-spacings of: 5.43, 4.59, 3.96, 3.64, 3.55, and 3.48 Å from an x-ray powder diffraction pattern obtained using Cu radiation.

Compound I Form A is also characterized by differential scanning calorimetry (DSC). The DSC curve for Compound I Form A is characterized by an endotherm with a peak temperature of 238.5° C.±2° C.

EXAMPLE 3

Preparation of the Fumarate Salt of Compound I

Compound I (1.60 g) was dissolved in EtOAc (200 mL) under reflux, and the resulting solution was cooled to 50° C. A solution of fumaric acid (0.58 g) in EtOH (20 mL) was added to the Compound I solution, and the mixture was stirred at room temperature overnight. The resulting crystals were isolated by filtration and the vessel and cake were washed with EtOAc (50 mL), and dried in vacuo at 40° C. for 2 h to obtain the fumarate salt of Compound I as colorless crystals. $^1$H NMR (300 MHz, DMSO-$d_6$): 13.14 (brs, 2H), 10.83 (s, 1H), 9.13 (d, J=0.8 Hz, 1 H), 8.89 (d, J=4.9 Hz, 1 H), 8.11 (t, J=2.6 Hz, 1H), 7.87 (dd, J=5.0, 1.1 Hz, 1H), 7.78-7.72 (m, 1H), 7.49-7.31 (m, 3H), 6.91 (d, J=2.6 Hz 1H), 6.62 (s, 2H), 2.80-2.76 (m, 1H), 2.19-1.86 (m, 8H).

TABLE 4

Powder X-ray diffraction: Compound I Fumarate Salt

| 2θ(2 theta)(degrees) | Intensity(cps) | d-spacing (A) |
|---|---|---|
| 9.592 | 100.00 | 9.212 |
| 16.316 | 35.62 | 5.428 |
| 16.675 | 55.23 | 5.312 |
| 17.417 | 38.08 | 5.087 |
| 18.565 | 65.92 | 4.775 |
| 19.292 | 37.46 | 4.596 |
| 22.192 | 29.69 | 4.002 |
| 25.953 | 30.83 | 3.430 |
| 26.645 | 61.29 | 3.342 |
| 28.390 | 61.40 | 3.141 |

Although the fumarate salt of Compound I is characterized by the complete group of angle 2 theta values listed in Table 4, all the values are not required for such identification. The fumarate salt of Compound I can be identified by the angle theta value in the range of 8.5-10.0°. The fumarate salt of Compound I can be identified by any one of the following angle theta values, or any one of the following groups of angle theta values:

a) 9.59°;
b) 9.6° and 18.6°
c) 9.6°, 18.6° and 28.4°
d) 9.6°, 18.6°, 28.4°, and 26.6°
e) 9.6°, 16.7°, 18.6°, 28.4°, and 26.6°
f) 9.6°, 16.7°, 18.6°, 28.4°, 26.6°, 17.4°, 19.3°, 16.3°, 25.9°, and 22.2°

Additionally, each of the angle 2 theta values from Table 4 can be expressed to two decimal places as follows: 9.59°, 16.31°, 16.67°, 17.41°, 18.56°, 19.29°, 22.19°, 25.95°, 26.64°, and 28.39°.

The fumarate salt of Compound I can also be identified by one or more reflections at d-spacings of: 9.21, 5.43, 5.31, 5.09, 4.77, 4.59, 4.00, 3.43, 3.34, and 3.14 Å from an x-ray powder diffraction pattern obtained using Cu radiation.

EXAMPLE 4

Preparation of the Mesylate Salt of Compound I

Compound I (3.90 g) was dissolved in EtOAc (200 mL) under reflux and the resulting solution was cooled to 50° C. A solution of methanesulfonic acid (0.94 g) in EtOH (10 mL) was added to the Compound I solution, and the mixture was stirred at room temperature overnight. The resulting crystals were isolated by filtration and the vessel and cake were washed with EtOAc (100 mL), and dried in vacuo at 40° C. for 2 h to obtain the mesylate salt of Compound I as yellow crystals. $^1$H NMR (300 MHz, DMSO-$d_6$): 10.81 (s, 1H), 9.14 (d, J=1.1 Hz, 1 H), 8.90 (d, J=5.0 Hz, 1 H), 8.11 (t, J=2.6 Hz, 1H), 7.88 (dd, J=5.0, 1.1 Hz, 1H), 7.78-7.71 (m, 1H), 7.49-7.31 (m, 3H), 6.90 (d, J=2.6 Hz 1H), 2.82-2.78 (m, 1H), 2.33 (s, 3H), 2.17-1.86 (m, 8H).

TABLE 5

Powder X-ray diffraction: Compound I Mesylate Salt

| 2θ(2 theta)(degrees) | Intensity(cps) | d-spacing (A) |
|---|---|---|
| 10.564 | 37.96 | 8.366 |
| 16.068 | 74.50 | 5.511 |
| 17.159 | 37.37 | 5.163 |
| 17.919 | 76.53 | 4.946 |
| 19.905 | 100.00 | 4.456 |
| 22.258 | 54.04 | 3.990 |
| 23.561 | 39.97 | 3.772 |
| 23.837 | 33.31 | 3.729 |
| 26.668 | 35.40 | 3.339 |
| 28.775 | 51.05 | 3.099 |

Although the mesylate salt of Compound I is characterized by the complete group of angle 2 theta values listed in Table 5, all the values are not required for such identification. The mesylate salt of Compound I can be identified by the angle theta value in the range of 19.5-20.0°. The mesylate salt of Compound I can be identified by any one of the following angle theta values, or any one of the following groups of angle theta values:

a) 19.90°;
b) 19.9° and 17.9°
c) 19.9°, 17.9° and 16.1°
d) 19.9°, 17.9°, 16.1°, and 22.3°
e) 19.9°, 17.9°, 16.1°, 22.3° and 28.8°
f) 19.9°, 17.9°, 16.1°, 22.3°, 28.8°, 23.6°, 10.6°, 17.2°, 26.7°, and 23.8°

Additionally, each of the angle 2 theta values from Table 5 can be expressed to two decimal places as follows: 10.56, 16.07, 17.16, 17.92, 19.90, 22.26, 23.56, 23.84, 26.67, and 28.77.

The mesylate salt of Compound I can also be identified by one or more reflections at d-spacings of: 8.37, 5.51, 5.16, 4.95, 4.46, 3.99, 3.77, 3.73, 3.34, and 3.09 Å from an x-ray powder diffraction pattern obtained using Cu radiation.

What is claimed is:

1. A process for preparing a compound of formula I, or a salt or polymorph thereof, wherein the salt is the mesylate or fumarate salt and the polymorph is pure Form A or Form C, comprising the step of coupling a compound of formula II with a compound of formula III, or a salt thereof, in the presence of SOCl$_2$ and dimethylacetamide, wherein the mesylate salt of Compound I has an x-ray powder diffraction pattern obtained using Cu radiation containing an angle 2 theta value of 19.90°;

wherein the fumarate salt of Compound I has an x-ray powder diffraction pattern obtained using Cu radiation containing an angle 2 theta value of 9.59°;

wherein pure Form A of Compound I has an x-ray powder diffraction pattern obtained using Cu radiation containing an angle 2 theta value of 22.42°; and wherein Form C of Compound I has an x-ray powder diffraction pattern obtained using Cu radiation containing an angle 2 theta value of 27.0-28.0°.

2. The process of claim 1 further comprising isolating the compound of formula I by crystallizing from dimethylformamide/methanol/water or dimethylacetamide/water.

3. A compound which is crystalline Form C of Compound I having an x-ray powder diffraction pattern obtained using Cu radiation containing an angle 2 theta value of 27.0-28.0°.

4. The compound of claim 3 having an x-ray powder diffraction pattern obtained using Cu radiation containing an angle 2 theta value of 27.59°.

5. The compound of claim 3 having an x-ray powder diffraction pattern obtained using Cu radiation containing the following angle 2 theta values: 27.6° and 17.5°.

6. The compound of claim 3 having an x-ray powder diffraction pattern obtained using Cu radiation containing the following angle 2 theta values: 27.6°, and 17.5°, and at least one angle theta value selected from the group consisting of: 23.8°, 21.5°, 14.9°, 17.7°, and 20.2°.

7. The compound of claim 3 having an x-ray powder diffraction pattern obtained using Cu radiation characterized by a reflection at a d-spacing of 5.95 Å.

8. The compound of claim 3 having an x-ray powder diffraction pattern obtained using Cu radiation characterized by a reflection at a d-spacing of 5.95 Å, and at least one reflection at a d-spacing selected from the group consisting of: 5.07 Å, 5.00 Å, 4.40 Å, 4.13 Å, 3.74 Å, and 3.23 Å.

9. The compound of claim 3 having an x-ray powder diffraction pattern obtained using Cu radiation characterized by reflections at d-spacings of about 3.2, 5.1 and 3.7 angstroms.

10. The compound of claim 9 further comprising an x-ray powder diffraction pattern obtained using Cu radiation characterized by reflections at d-spacings of about 4.1, 5.9 and 5.0 angstroms.

11. The compound of claim 10 further comprising an x-ray powder diffraction pattern obtained using Cu radiation characterized by reflections at d-spacings of about 4.40 angstroms.

12. The compound of claim 3 having a differential scanning calorimetry (DSC) peak melting temperature of about 216.7° C.

13. The compound of claim 3 characterized by the carbon-13 cross-polarization magic-angle spinning nuclear magnetic resonance spectrum of FIG. 5.

14. A pharmaceutical composition comprising a therapeutically effective amount of the crystalline Form C of Compound I of claim 3, and a pharmaceutically acceptable carrier.

15. A method of treating obesity in a subject in need thereof comprising administering to the subject a therapeutically effective amount of the crystalline Form C of Compound I of claim 3.

16. The compound of claim 3 prepared by a process comprising the steps of:
   (a) dissolving the compound of formula I in dimethylformamide to form a mixture;
   (b) heating the mixture of step (a) to about 50-55° C.;
   (c) filtering the mixture of step (b) to form a solution;
   (d) adding methanol to the solution of step (c) to give a solution;
   (e) seeding the solution of step (d) with one or more crystals of compound I form C;
   (f) aging the solution of step (e) at about 48-50° C.; and
   (g) adding deionized water to the solution of step (f).

17. A compound which is pure crystalline Form A of Compound I (I)

having an x-ray powder diffraction pattern obtained using Cu radiation containing an angle 2 theta value of 22.42°.

18. A compound which is the mesylate salt of Compound I (I)

having an x-ray powder diffraction pattern obtained using Cu radiation containing an angle 2 theta value of 19.90°.

19. A compound which is the fumarate salt of Compound I (I)

having an x-ray powder diffraction pattern obtained using Cu radiation containing an angle 2 theta value of 9.59°.

* * * * *